US 7,829,103 B2

(12) United States Patent
Pethe et al.

(10) Patent No.: US 7,829,103 B2
(45) Date of Patent: Nov. 9, 2010

(54) METHYLATED HEPARIN-BINDING HEMAGGLUTININ RECOMBINANT MYCOBACTERIAL ANTIGEN, PREPARATION METHOD AND IMMUNOGENIC COMPOSITIONS COMPRISING SAME

(75) Inventors: Kevin Pethe, La Madeleine (FR); Franco Menozzi, Hyon (BE); Camille Locht, Brussels (BE)

(73) Assignees: Institut Pasteur de Lille, Lille Cedex (FR); Institut National de la Sante Et de la Rechereche Medicale, Paris (FR)

( * ) Notice: Subject to any disclaimer, the term of this patent is extended or adjusted under 35 U.S.C. 154(b) by 962 days.

(21) Appl. No.: 10/847,606

(22) Filed: May 18, 2004

(65) Prior Publication Data

US 2006/0292168 A1 Dec. 28, 2006

Related U.S. Application Data

(63) Continuation of application No. PCT/FR02/03942, filed on Nov. 18, 2002.

(30) Foreign Application Priority Data

Nov. 19, 2001 (FR) .................................. 01 14953

(51) Int. Cl.
*A61K 39/04* (2006.01)
*A61K 39/02* (2006.01)
*A61K 49/00* (2006.01)

(52) U.S. Cl. ...................... 424/248.1; 424/9.1; 424/9.2; 424/184.1; 424/185.1; 424/190.1; 424/200.1; 424/234.1; 424/278.1; 530/300; 530/350

(58) Field of Classification Search .................. 424/9.1, 424/9.2, 184.1, 185.1, 190.1, 200.1, 234.1, 424/248.1, 278.1; 530/300, 350
See application file for complete search history.

(56) References Cited

U.S. PATENT DOCUMENTS 5,717,064 A 2/1998 Julian et al.

FOREIGN PATENT DOCUMENTS

WO WO 97/44463 A2 11/1997

OTHER PUBLICATIONS

Menozzi, F.D., et al. "Identification of a Heparin-binding Hemagglutinin Present in Mycobacteria", J. Exp. Med., vol. 184, pp. 993-1001, Sep. 1996.*
F. D. Menozzi et al., Proc Natl Acad Sci USA, Oct. 13, 1998, 95(21):12625-12630.
Pethe et al: "Mycobacterial heparin-binding hemagglutinin and laminin-binding protein share antigenic methyllysines that confer resistance to proteolysis" Proceedings of the National Academy of Sciences, USA, vol. 99, Aug. 6, 2002, pp. 10759-10764.
Pethe et al: "Functional and immunological characterizations of the lysine-rich repeats in the C-terminal domain of the mycobacterial heparin-binding hemagglutinin" Abstracts of the General Meeting of the American Society for Microbiology, The Society, Washington, DC, US, vol. 99, No. 231/U-106, May 30, 1995, p. 654.
Poncz et al: "The resistance to tryptic hydrolysis of peptide bonds and adjacent to Ne, N-dimethyllysyl residues" Journal of Biological Chemistry, vol. 258, Feb. 10, 1983, pp. 1844-1850.
Pethe et al: "Characterization of the heparin-binding site of the mycobacterial heparin-binding hemagglutinin adhesin" Journal of Biological Chemistry, vol. 275, May 12, 2000, pp. 14273-14280.
Joys et al: "The susceptibility to tryptic hydrolysis of peptide bonds involving epsilon-N-methyllysine" Biochimica et Biophysica Acta, No. 581, 1979, pp. 360-362.

* cited by examiner

*Primary Examiner*—Rodney P. Swartz
(74) *Attorney, Agent, or Firm*—Birch, Stewart, Kolasch & Birch, LLP.

(57) ABSTRACT

The invention concerns a methylated immunogenic recombinant peptide sequence comprising mycobacterial heparin-binding hemagglutinin. The invention also concerns chemical and enzymatic methods for preparing such a sequence, the sequence being previously produced in a non-methylated recombinant form then methylated by post-translational modification. The invention further concerns recombinant tools, vectors and host cells for implementing post-translational enzymatic methylation of the recombinant HBHA. The invention finally concerns immunogenic compositions comprising methylated, native or recombinant HBHA, such compositions being useful for preparing vaccines against mycobacterial infections.

20 Claims, 5 Drawing Sheets

SEQUENCE LISTING

```
<160> NUMBER OF SEQ ID NOS: 1

<210> SEQ ID NO 1
<211> LENGTH: 39
<212> TYPE: PRT
<213> ORGANISM: Mycobacterium tuberculosis

<400> SEQUENCE: 1

Lys Lys Ala Ala Pro Ala Lys Lys Ala Ala Pro Ala Lys Lys Ala Ala
1               5                   10                  15

Pro Ala Lys Lys Ala Ala Ala Lys Lys Ala Pro Ala Lys Lys Ala Ala
            20                  25                  30

Ala Lys Lys Val Thr Gln Lys
        35
```

METHYLATED HEPARIN-BINDING HEMAGGLUTININ RECOMBINANT MYCOBACTERIAL ANTIGEN, PREPARATION METHOD AND IMMUNOGENIC COMPOSITIONS COMPRISING SAME

This application is a Continuation of co-pending PCT International Application No. PCT/FR02/03942 filed on Nov. 18, 2002, which designated the United States, and on which priority is claimed under 35 U.S.C. §120, and 35 U.S.C. §119(a) on Patent Application No(s). 0114953 filed in France on Nov. 19, 2001, the entire contents of which are hereby incorporated by reference.

The present invention relates to the field of research and development of novel vaccines for the treatment of mycobacterial infections, in particular tuberculosis.

The invention concerns a methylated immunogenic recombinant peptide sequence corresponding to heparin-binding hemagglutinin (HBHA) identified in mycobacterial strains such as *Mycobacterium tuberculosis* and *M. bovis* BCG (Menozzi et al 1996 J Exp Med 184:993-1001).

The invention also concerns methods for preparing an immunogenic peptide sequence comprising recombinant HBHA, said sequence being methylated by post-translational modification. In particular, the invention concerns methods for chemical or enzymatic methylation of a peptide sequence comprising HBHA and produced in a nonmethylated recombinant form.

The invention also concerns recombinant host cells, tools and vectors for carrying out the post-translational methylation of recombinant HBHA by chemical or enzymatic methods.

Finally, the invention concerns immunogenic compositions comprising methylated HBHA, native or recombinant, said compositions being used to prepare vaccines against mycobacterial infections.

*Mycobacteria* are bacillae with a highly diversified habitat. Depending on the species, such bacteria can colonize the ground, water, plants, animals and/or humans. Certain species such as *M. smegmatis* are non pathogenic saprophytes. Other species, however, are pathogenic to animals and/or humans to a greater or lesser extent. Thus *M. avium* causes infections in birds. *M. bovis* is responsible for bovine tuberculosis, and has also been implicated in cases of human tuberculosis. In humans, tuberculosis is principally caused by the highly pathogenic species *M. tuberculosis*. *M. leprae* is responsible for leprosy, another human disease which is rampant in developing countries.

Currently, tuberculosis is still a major public health problem as it has the highest mortality for a single infectious agent. The World Health Organization (WHO) recorded 8.8 million cases of tuberculosis in 1995 (Dolin et al 1994 Bull WHO 72: 213-220). More recently, WHO published alarming figures disclosing 10 million new cases of tuberculosis per year, killing 3 million people per year (Dye et al 1999 J Am Med Assoc 282: 677-686). It is estimated that one third of the world's population is infected with *M. tuberculosis*. However, not every infected person develops the disease.

The problems raised by tuberculosis were exacerbated in the 1980s with the emergence of the pandemic due to acquired immunodeficient syndrome (AIDS). The number of cases of tuberculosis associated with immunodepression caused by the HIV retrovirus, responsible for AIDS, has not ceased to grow.

To be effective, drug treatment of tuberculosis generally has to be prolonged, especially in patients already infected with the HIV virus. In the past *M. tuberculosis* infections were effectively wiped out with certain antibiotics, including rifampicin, isoniazide and pyrazinamide. However, antibiotic therapies rapidly reached their limits in the curative treatment of tuberculosis, firstly due to the emergence of antibiotic-resistant strains of *M. tuberculosis*, in particular to isoniazide, and secondly due to the toxicity of certain anti-tuberculosis molecules, including pyrazinamide.

Only one vaccine is authorized and has been in current use for more than 75 years to prevent tuberculosis infection. It is the Calmette and Guérin bacillus, known as the BCG vaccine. That vaccine consists of a live form of a strain of *M. bovis* isolated in 1908 from a cow and rendered avirulent in vitro to allow parenteral administration to humans. However, that vaccine is currently the subject of controversy as it is limited, in particular as regards efficacy. According to the many clinical trials carried out around the world, the protective efficacy obtained using the BCG vaccine is from 0 to 85% (Fine, P E, 1989 Rev Infect Dis 11 Suppl 2: S353-S359). A meta-analysis suggests that the mean efficacy of BCG would not exceed 50% protection against pulmonary tuberculosis (Colditz et al, 1994, Jama 271: 698-702). Further, the BCG vaccine has been shown to be relatively effective in children, while its protective effect is virtually zero in the adult. Further again, because the BCG vaccine consists of a live mycobacterial strain, its administration is not free from side effects on the human organism, even though it is an attenuated strain. Such side effects appearing a fortiori in immunodeficient patients, vaccinating such patients is to be avoided. That problem cannot be overcome by killing and inactivating BCG, because they would lose any protective effects (Orme I M, 1988, Infect. Immun 56: 3310-3312).

Thus, the present invention aims to overcome the disadvantages of the BCG vaccine by proposing a novel immunogenic composition that can be used as a vaccine against tuberculosis. This immunogenic composition can also be used in a more general manner in the context of the prevention of mycobacterial infections.

Tuberculosis is a contact disease which is transmitted by air. Once inhaled, *M. tuberculosis* germs travel to the lungs which constitute the initial center of infection. From the lungs, the germs are rapidly disseminated through the blood or lymphatic system to other regions of the organism.

The entire sequence of the genome for the current best characterized *M. tuberculosis* strain, namely H37Rv, has been determined and analyzed to increase our knowledge regarding the biology of this pathogen and to identify new targets that could be used to develop novel therapeutic treatments, i.e., prophylactic or curative treatments (Cole et al, 1998, Nature 393: 537-544). The current approach consists of creating genomic libraries from the DNA of *M. tuberculosis* and screening those libraries to identify novel potential therapeutic targets. Interestingly, it has been observed that *M. tuberculosis* strains exhibit a high genetic homogeneity, the nucleotide changes from one sequence to another being very rare. Further, the majority of the proteins are identical across the strains of this species. This is particularly important as regards immunity and the development of vaccines, as the antigenic markers to be screened are almost ubiquitous.

Despite the high incidence of mycobacterial infections, little is known about the primary molecular mechanisms involved in their pathogenesis.

One of the major events in the pathogenesis of tuberculosis is the adhesion of microorganisms to target cells. Alveolar macrophages have long been considered to be the portal of entry for *M. tuberculosis* and are assumed to transport the bacteria from the lungs to the other organs. However, it has recently been shown that *M. tuberculosis* is also able of interacting with epithelial cells, including M cells, which could allow the bacillus to directly cross the epithelial barrier (Teitelbaum et al, 1999 Immunity 10: 641-650). The relative contribution of each of these mechanisms as well as the bacterial factors involved in extra-pulmonary dissemination of *M. tuberculosis* is still unknown.

*M. tuberculosis* strains produce an adhesin termed HBHA (heparin-binding hemagglutinin adhesion) on their surface (Menozzi et al, 1996 J Exp Med 184: 993-1001). That protein is also produced by other pathogenic mycobacteria, such as *M. leprae* and *M. avium* (Reddy et al, 2000 J Infect Dis 181: 1189-1193). In contrast, HBHA is not produced by the non pathogenic saprophyte species *M. smegmatis* (Pethe et al, 2001 Mol Microbiol 39: 89-99).

Binding of *M. tuberculosis* to epithelial cells is inhibited by anti-HBHA antibodies or by competition with heparin. This is not the case with macrophages, and so that observation suggests that the adhesion conferred by HBHA is specific to non phagocyte cells. The mechanism for this adhesion relies on recognition, by the lysine-rich carboxy terminal domain of HBHA (Pethe et al, 2000 J Biol Chem 275: 14273-14280), of receptors containing sulphated glycosaminoglycans carried by the epithelial cells.

More recently, studies have shown that HBHA plays neither a preponderant role in the initial steps of tuberculosis infection, nor in the persistence of mycobacteria in the lungs (Pethe et al, 2001 Nature 412: 190-194). That team also showed that HBHA was not required for colonization and survival in the spleen. In contrast, HBHA plays a crucial role in extra-pulmonary mycobacterial dissemination. Consequently, that adhesin is a virulence factor, the binding of which to non-phagocytary cells represents an essential step in the dissemination of mycobacteria from the lungs to the spleen and potentially to other organs such as the liver, bones, the kidneys or, possibly, the brain.

The present invention is aimed at using the antigenic power of HBHA within the context of an essentially prophylactic treatment, the role of HBHA being of primary importance in the dissemination of microorganisms in infected subjects.

The cloning of the gene encoding HBHA and its expression in *Escherichia coli* have suggested that the protein undergoes post-translational modification (Menozzi et al, 1998 Proc Natl Acad Sci USA, 95: 12625-12630). In that publication, the authors hypothesized that native HBHA could be glycosylated, which hypothesis was subsequently shown to be inexact. More recent work has shown that the only covalent post-translational modification undergone by the HBHA produced by *M. tuberculosis* is a complex methylation of lysine residues contained in the carboxy-terminal domain of the protein.

Within the context of the present invention, the inventors show the nature of the post-translational modification carried by the native HBHA, namely a complex covalent methylation, said modification endowing it with a protective antigenic power against mycobacterial infections. The peptide sequence of the recombinant HBHA produced after expressing its gene in *E. coli*, for example, exhibits no protective activity, as it does not undergo post-translational modification, like native HBHA.

Thus, the invention concerns an immunogenic recombinant peptide sequence comprising a methylated antigen corresponding to native HBHA or to the C-terminal portion thereof.

Within the context of the present invention, the term "peptide sequence" designates all or a portion of the sequence for the HBHA protein, provided that said "peptide sequence" contains at least the lysine-rich carboxy-terminal region which ensures heparin binding. The sequence for said carboxy-terminal region is as follows:

KKAAPAKKAAPAKKAAPAKKAAAKKAPA-KKAAAKKVTQK (SEQ ID NO: 1)

This sequence was disclosed in the International patent publication with publication number WO 97/44463.

The term "protein", "HBHA protein" or "HBHA" as used in the present invention means all or a portion of the peptide sequence for HBHA, provided that it includes at least the C-terminal region of said HBHA. When the sequence under consideration comprises at most the C-terminal region of the HBHA, the term "peptide" will advantageously be used. The term "peptides" will be used to designate products from the enzymatic digestion of HBHA. However, the use of the term "peptide" is not limited to this instance, "peptide" also being synonymous with "protein" within the context of the invention.

A "recombinant" peptide sequence in accordance with the invention corresponds to a peptide sequence obtained by expression, in a heterologous cell host, of a nucleotide sequence encoding said peptide sequence. In particular, said heterologous cell host can be a bacterium that does not belong to the *Mycobacterium* genus, for example *E. coli*, or other organisms such as yeasts or animal or plant cells.

The expression "nucleotide sequence" designates any DNA sequence encoding a peptide sequence as defined in the context of the present invention.

In accordance with accepted use, an "antigen" designates any peptide sequence of the present invention having an immunogenic power. In particular, an antigen of the invention could be restricted to the carboxy-terminal heparin binding region of HBHA.

Within the context of the invention, the expressions "heparin-binding carboxy-terminal region", "heparin-binding region", "carboxy-terminal region" and "C-terminal region" of HBHA designates the same region of said HBHA, the sequence for which is given above. Thus, these expressions are equivalent.

Preferably, the immunogenic recombinant peptide sequence of the present invention is methylated at the heparin-binding region of the HBHA. In particular, the methyl groups are carried by lysine residues present in said heparin-binding region.

In a more preferred embodiment of the present invention, the methyl groups are carried by all or only part of the lysine residues present in the C-terminal region of HBHA, provided that the methylated peptide sequence has an immunogenic activity.

Advantageously, at least thirteen lysine residues out of the fifteen present in the C-terminal region are methylated. The two non-methylated lysine residues are the amino acids distal to the sequence indicated above for the C-terminal region of the HBHA.

The methylated lysine residues are preferably mono- or di-methylated.

In the publication by Menozzi et al, 1998, supra, it was also shown that native HBHA was recognized by two monoclonal antibodies, namely 3921E4 and 4057D2 (Rouse et al, 1991 Infect Immun 59: 2595-2600), while the recombinant form of HBHA not post-translationally modified was not recognized by antibody 4057D2, indicating that one of the epitopes of native HBHA was absent from recombinant HBHA.

The immunogenic recombinant peptide sequence of the present invention, namely the recombinant form of HBHA methylated in a post-translational manner, is recognized by the monoclonal antibody 4057D2, in contrast to the non methylated recombinant form of said HBHA, as will be described in the examples below.

The invention also concerns methods for preparing an immunogenic peptide sequence comprising recombinant HBHA, said sequence being methylated by post-translational modification.

In particular, a preparation method of the present invention comprises at least the following steps:
    a) producing the recombinant HBHA protein in a heterologous host cell—this form of HBHA being non methylated;
    b) purifying said protein using conventional methods; and
    c) post-translational methylation of the purified recombinant HBHA.

It is understood that in the context of the invention, the HBHA protein purification step can be carried out before or, in another embodiment, after the protein methylation step.

The preparation method of the invention can produce methylated recombinant HBHA protein or, alternatively, any methylated peptide comprising at least the heparin-binding region of said protein. In particular, said methylated peptide obtained by the method of the invention corresponds to said heparin-binding region of the HBHA.

Advantageously, the heterologous host cell used in the preparation method of the invention is a bacterium, in particular *E. coli* or *M. smegmatis*. In particular, the host used is *M. smegmatis*.

Protein purification methods are known to the skilled person and do not form part of the present invention per se. As an example, the heparin-binding properties conferred by the C-terminal region of HBHA can be exploited by purifying said HBHA by affinity on a heparin-sepharose column (Pethe et al, 2000, supra).

In particular, the invention concerns methods for chemical and enzymatic methylation of a peptide sequence comprising HBHA previously produced in a nonmethylated recombinant form.

The term "production in a recombinant form" means producing a peptide by expression in any heterologous prokaryotic or eukaryotic host. Production can be carried out from a cell culture or in vivo, such as in milk or in a plant.

The chemical methylation of the invention is derived from the literature (Means G E, 1977 Meth Enzymol 47: 469-478). In particular, the chemical methylation reaction is carried out in a solution comprising formaldehyde and $NaBH_4$.

The enzymatic methylation methods of the invention can be carried out using one or more mycobacterial methyltransferases. Said methyltransferases catalyze the transfer of methyl groups from a donor to an acceptor, in this instance the peptide sequence for the previously purified recombinant HBHA. The methyl radical donor can be S-adenosylmethionine (AdoMet), which is well known to the skilled person.

More particularly, the methyltransferase or methyltransferases are present and active in extracts from total mycobacterial proteins such as *M. bovis* BCG or *M. smegmatis*.

In a further embodiment of the present invention, the mycobacterial methyltransferase or methyltransferases are purified from total protein extracts from mycobacterial strains, before being placed in the reaction medium to catalyze the transmethylation reaction or reactions from the donor to the acceptor.

The invention also concerns recombinant host cells, vectors and tools for carrying out the enzymatic post-translational methylation of recombinant HBHA.

In particular, the invention concerns a recombinant host cell that can co-express nucleotide sequences encoding HBHA and mycobacterial methyltransferase(s). Said host cell is preferably a bacteria, in particular a strain of *E. coli*.

The term "co-express" as used in the present invention means the faculty of a given host cell to express at least two distinct nucleotide sequences.

In one embodiment of the present invention, the host cell is characterized in that it simultaneously holds at least two recombinant vectors, one of which encodes HBHA while the other(s) encode the mycobacterial methyltransferase(s).

In particular, the host cell of the invention holds as many recombinant vectors as there are different proteins to be produced, each vector then encoding a distinct recombinant mycobacterial protein.

The terms "vector", "expression vector" and "plasmid" are used in the context of the present invention to designate the same cloning tool and expression of nucleotide sequences in a manner that is conventional for the skilled person.

In a further embodiment of the invention, all of the recombinant mycobacterial proteins or only a part thereof are encoded by the same expression vector.

In particular, the host cell holds a single expression vector from which all of the mycobacterial proteins are produced, namely HBHA and the methyltransferase or methyltransferases.

When the host cell holds a single vector, the production of each mycobacterial protein, HBHA or methyltransferase, is controlled by distinct regulation sequences or, in a further embodiment, by the same regulation sequences.

In particular, the production of all or a part of the recombinant proteins is controlled by the same regulation sequences.

An expression vector of the present invention advantageously encodes HBHA and at least one mycobacterial methyltransferase.

Alternatively, an expression vector of the invention encodes a single recombinant mycobacterial protein selected from HBHA and the methyltransferase or methyltransferases.

The present invention concerns not only the host cells and the expression vectors as defined above considered per se, but also implementation of the enzymatic methylation methods of the invention.

The present invention also pertains to a method for producing an immunogenic peptide sequence comprising recombinant HBHA, said sequence being methylated by post-translational modification, said method comprising at least the following steps:
    a) co-producing the HBHA protein and the mycobacterial methyltransferase or methyltransferases by a host cell as defined above;
    b) post-translational methylation of the recombinant HBHA by the recombinant methyltransferase or methyltransferases; and
    c) purifying the methylated recombinant HBHA using conventional methods.

The invention also concerns methylated immunogenic recombinant peptide sequences that can be obtained in vivo using an enzymatic method or in vitro using a chemical or enzymatic method.

Finally, the invention concerns immunogenic compositions comprising methylated HBHA, native or recombinant, said compositions being used to prepare vaccines against mycobacterial infections.

In particular, an immunogenic composition of the present invention comprises, in a pharmaceutically acceptable formulation, an active principle which is a methylated peptide sequence selected from the peptide sequence for native HBHA and the peptide sequence for recombinant HBHA.

A "pharmaceutically acceptable formulation" as used in the present invention corresponds to a drug formulation that can be used in humans in acceptable in vivo doses having regard to the toxicity and pharmacology of the compounds concerned, while being effective on a therapeutic level, in particular on an immunogenic level.

In a preferred embodiment of the invention, the methylated peptide sequence acting as the active principle is associated with one or more adjuvants.

The term "adjuvant" or "adjuvant compound" as used in the present invention means a compound that can induce or increase the specific immune response towards an antigen or immunogen, said response consisting of a humoral and/or cellular response. Said immune response generally occurs via stimulation of the synthesis of specific immunoglobulins for a given antigen, in particular IgG, IgA and IgM, or of cytokines.

The active principle, methylated HBHA peptide sequence, as well as the adjuvant or adjuvants are generally mixed with pharmaceutically acceptable excipients such as water, a saline buffer, dextrose, glycerol, ethanol, or mixtures thereof. Said immunogenic compositions are prepared in the form of liquid solutions or injectable suspensions or in the solid form, for example freeze dried, suitable for dissolution prior to injection.

An immunogenic composition of the present invention is formulated to allow administration by diverse routes such as nasally, orally, sub-cutaneously, intradermally, intramuscularly, vaginally, rectally, ocular, or auricular. In particular, the choice of auxiliary compounds is dictated by the selected mode of administration. Said auxiliary compounds can in particular be wetting agents, emulsifying agents or buffers.

Advantageously, an immunogenic composition of the invention comprises, per dose, 0.1 to 20 µg, preferably 5 µg of purified HBHA protein.

BRIEF DESCRIPTION OF THE DRAWINGS

The present invention is illustrated in a non-limiting manner in the accompanying figures in which.

Figure 1A:
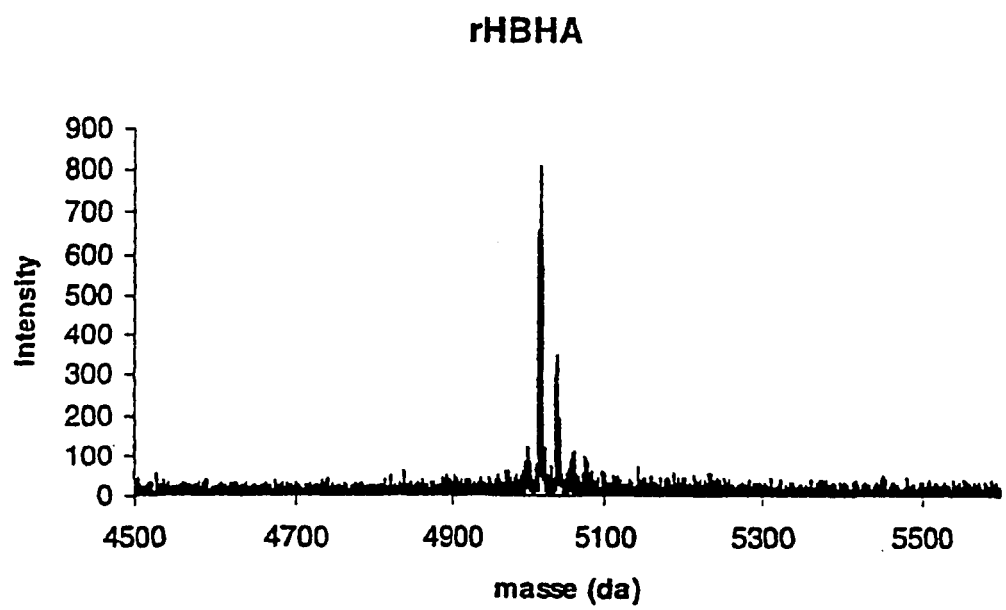
FIG. 1 shows the determination of the mass of the peptide corresponding to the heparin-binding region of native and recombinant HBHA. Said HBHAs were digested overnight with Endoproteinase Glu-C (Endo-GLu; EC3.4.24.33). The fragments corresponding to the heparin-binding region were purified by HPLC. The fragment weight of recombinant HBHA (A) and native HBHA (B) were then analyzed by mass spectroscopy.

The invention will be better understood from the following detailed description which is given purely by way of illustration. It should be understood that the present invention is not in any way limited to examples figuring in the detailed description.

DETAILED DESCRIPTION OF THE INVENTION

I—Materials and Methods

I-1—Bacterial Strains and Culture Conditions

Strains of *M. bovis* BCG 1173P2 (OMS), *M. tuberculosis* MT103 and *M. smegmatis* MC$^2$155 were cultivated in Sauton medium (Menozzi et al 1996 supra). The *E. coli* BL21(DE3) pET-hbha strain (Pethe et al, 2000, supra) was cultivated in LB medium supplemented with 30 µg/ml of kanamycin.

I-2—Purification of HBHA

Native and recombinant HBHA were isolated as described (Menozzi et al, 1996, supra; Pethe et al, 2000, supra). The final purification step was carried out using reverse phase HPLC (Beckman Gold system) using a nucleosyl-C18 type column equilibrated in 0.05% trifluoroacetic acid. Elution was carried out using a linear gradient of 0 to 80% acetonitrile prepared in 0.05% trifluoroacetic acid.

I-3—Analysis of Peptides or Proteins by Mass Spectrometry

The samples (0.1 to 10 picomoles) were prepared by the "dry drop" method.

For peptides, a 0.5 µl volume of solution was mixed with α-cyano-4-hydroxycinnamic acid extemporaneously dissolved in an amount of 10 mg/ml in a solution containing 50% $CH_3CN$ and 0.1% trifluoroacetic acid. After depositing on the analytical plate, the samples were dried. Mass spectrometry analyses were carried out using a MALDI-TOF Voyager-DE-STR type apparatus (Applied BioSystems, Foster City, Calif.). Deposits containing peptides of less than 3000 Da were analyzed using the following parameters: positive and reflector modes, acceleration voltage 20 kV, screen tension 61%, delayed extraction 90 ns, and mass threshold less than 500 Da. For peptides of 3000 to 10000 Da, the parameters were: positive and reflector modes, acceleration voltage 25 kV, screen tension 65%, delayed extraction 250 ns, and mass threshold less than 1000 Da. The spectra were calibrated externally from monoisotopic ions [M+H$^+$] of different peptides.

For proteins, a 0.5 µl sample was mixed with sinapinic acid extemporaneously dissolved in an amount of 10 mg/ml in a solution containing 50% $CH_3CN$ and 0.1% trifluoroacetic acid. After deposition and drying, mass spectrometry analyses were carried out using the following parameters: positive and linear modes, acceleration voltage 25 kV, grid tension 92%, delayed extraction 750 ns, and mass threshold less than 1000 Da. The spectra were calibrated externally from the mean masses of ions [M+H$^+$] of the thioredoxin of *E. coli* and of equine apomyoglobin (Applied BioSystems).

I-4—Digestion of Proteins by Endo-Glu and Peptide Separation 1 nanomole of lyophilized HBHA or recombinant HBHA purified by chromatography on heparin-sepharose followed by reverse phase HPLC was digested overnight in the presence of 5% Endo-Glu (Roche) in 100 nM of phosphate buffer (pH 8.0). After enzymatic digestion, the resulting peptides were separated by reverse phase HPLC using a Beckman Ultrasphere ODS type column (2×200 mm) in a linear elution gradient of 0 to 60% acetonitrile prepared in 0.1% trifluoroacetic acid.

I-5—Analysis of Amino Acids and Sequence Determination

To analyze the complete composition of amino acids, native HBHA purified by HPLC was hydrolyzed by heating constantly at 110° C. in a 6N HCl solution for 14 to 16 h. The amino acid composition was determined using a Beckman Gold System type analyzer. The amino-terminal peptide sequence was determined using the automated Edman degradation method using a pulsed liquid apparatus (Procise 492, Applied BioSystems) equipped with a 120 A amino acid analyzer. For each step in the sequence determination, the samples comprised 10 to 20 µl, which corresponded to a quantity of peptide of 250 to 500 picomoles.

I-6—Chemical Methylation of Lysine Residues

The method for chemical methylation of recombinant HBHA lysine residues was derived from the literature (Means, 1977, supra). In substance, recombinant HBHA purified on a heparin-sepharose column was dialyzed for 1 h at 4° C. against 250 volumes of 100 mM borate buffer (pH 9.0). After dialyis, 3 ml samples of 1 mg/ml protein solution were transferred into closed glass tubes containing 70 µl of a freshly prepared solution of 40 mg/ml $NaBH_4$ and 6 µl of 37% formaldehyde solution (formalin, Sigma, St Louis). The tubes were kept in ice. 200 µl samples were removed every ten minutes to verify the degree of completion of the methylation reaction by immunoblotting and mass spectrometry.

I-7—Enzymatic Methylation Test for Recombinant HBHA 100 ml of $M.$ $smegmatis$ or $M.$ $bovis$ BCG cultures with an optical density measured at 600 nm ($OD_{600}$) of 0.5 were centrifuged at 10000 g for 15 min. The pellet was re-suspended in 10 ml of 50 mM Hepes buffer (pH 7.4) containing 1 mM of AEBSF (Pefabloc Sc, Roche) and 15% (v/v) of glycerol (buffer A). The cells then underwent continuous sonication for 10 minutes at 4° C. using a Branson type sonicator, the outlet power being adjusted to 5. The total cell lysate was centrifuged at 4° C. at 20000 g for 15 min. For the methylation tests, 300 µl of total clarified lysate containing 1 mg of protein per ml was mixed with 40 µl of [methyl-$^{14}$C] AdoMet (60 mCi/mmol, Amersham Pharmacia Biotech), 100 µl of recombinant HBHA purified on a heparin column to 0.5 mg/ml, 5 µl of 1 M $MgCl_2$ and 55 µl of buffer A. The methylation tests were carried out at 25° C. 100 µl samples were removed at intervals to verify the degree of methylation of the recombinant HBHA by autoradiography.

I-8—Animals

The studies were carried out on eight week old female BALB/c mice (Iffa Credo, France). For infections with $M.$ $tuberculosis$, the mice were transferred into a type P3 confinement.

I-9—Immunization

The mice were immunized three times at two week intervals, subcutaneously at the base of the tail, with 5 µg of native HBHA per dose, emulsified or not emulsified in a solution of dimethyldioctadecylammonium (DDA, 150 µg/dose, Sigma) and monophosphorylated lipid A (MPL, 25 µg/dose, Sigma). At the moment of the first injection, one group of mice had received a subcutaneous BCG injection (Paris strain, $5×10^5$ CFU). The mice were infected ten weeks after the first immunization.

The same experiment was carried out, replacing the native HBHA with (i) nonmethylated recombinant HBHA and (ii) methylated recombinant HBHA in the doses for immunization.

I-10—Experimental Infections

As soon as the $OD_{600}$ reached 0.5, the $M.$ $tuberculosis$ cultures were washed once in Sauton medium, suspended in Sauton medium supplemented with 30% glycerol then divided into aliquots and finally frozen at −80° C. Prior to infection, an aliquot was defrosted, and the number of CFUs was determined. The mice were infected intravenously into the lateral vein of the tail using an inoculum of $10^5$ CFU of $M.$ $tuberculosis$ suspended in phosphate buffer (PBS, pH 7.4) in a final volume of 200 µl. Four mice per group were sacrificed after six weeks. The number of bacteria was determined in the spleen, liver and lungs of each infected mouse, spreading dilutions of the ground organs onto 7H11 medium.

The organs of mice vaccinated with BCG were spread onto 7H11 dishes containing 2 µg/ml of 2-thiophenecarboxylic acid hydrazide to inhibit the growth of residual BCG. The colonies were counted after incubating for two weeks at 37° C. The protective efficacy was expressed as the $log_{10}$ of the reduction in number of bacteria present in the organs of the immunized mice compared with the relative enumeration of the group which had received the adjuvant alone. The results were obtained from groups of four mice.

I-11—Lymphocyte Culture and IFN-γ-Assay

Spleen lymphocytes were purified as described (Andersen et al, 1991 Infect Immun 59: 1558-1563). Lymphocytes from four mice per experiment were cultured in 96 well plates (NUNC) containing $2×10^5$ cells/well in 200 µl of RPMI 1640 (Gibco, France) supplemented with 50 µM of 2-mercaptoethanol (Merck, Germany), 50 µg/ml of penicillin-streptomycin (Gibco), 1 mM of glutamax (Gibco) and 10% of foetal calf serum (Roche).

5 µg/ml of concanavalin A was used as the positive control for cell viability. Native HBHA was used in a final concentration of 5 µg/ml. The supernatants were recovered 72 hours after the start of stimulation in order to assay the IFN-γ. IFN-γ was detected using a sandwich type ELISA test. The anti-IFN-γ monoclonal antibodies used were obtained from R4-6A2 clones (Pharmingen, USA) for capture and SMG1-2 (Pharmingen) for detection.

II—Results and Examples

II-1—Characterization and Post-Translational Modification of Native HBHA

Figure 1B:
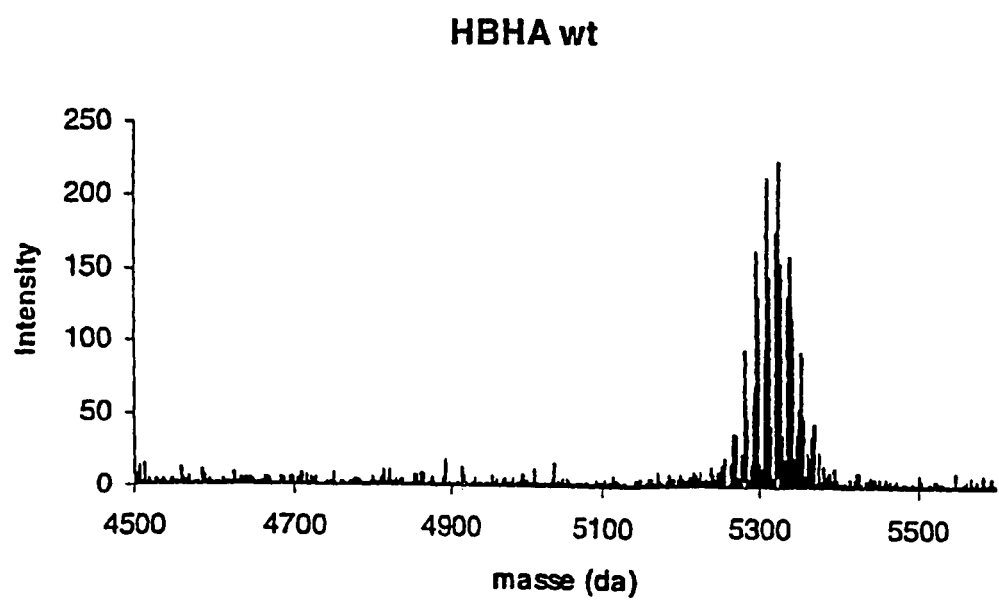

Mass spectrometry analysis showed that recombinant HBHA has a molecular weight (MW) of 21340, corresponding to the MW deduced from the nucleotide sequence encoding mycobacterial HBHA (hbhA gene or Rv0475 in $M.$ $tuberculosis$ H37Rv) (Menozzi et al, 1998, supra). In contrast, the MW for native HBHA was 21610, i.e. 270 more than recombinant HBHA. In consequence, the HBHA produced by the mycobacteria underwent a modification, which was not found in the recombinant protein produced by $E.$ $coli$. In order to define the exact nature of this modification, native and recombinant HBHA underwent hydrolysis with Endo-Glu and the mass of the peptides obtained was determined by mass spectrometry. The only difference between native and recombinant HBHA was identified at the carboxy-terminal region of said proteins. The mass of this region was 4342 for native HBHA and only 4076 for recombinant HBHA. This difference of about 270 Da corresponded to the mass difference measured between the entire HBHA proteins. Further, the post-translational modification or modifications to native HBHA could be localized to the C-terminal region. Further still, the mass spectrum corresponding to that region was constituted by a single peak for recombinant HBHA, while five peaks were present for native HBHA, those peaks being separated from each other by 14 Da (FIG. 1).

II-2—Determination of Post-Translational Modification of Native HBHA

Figure 2:
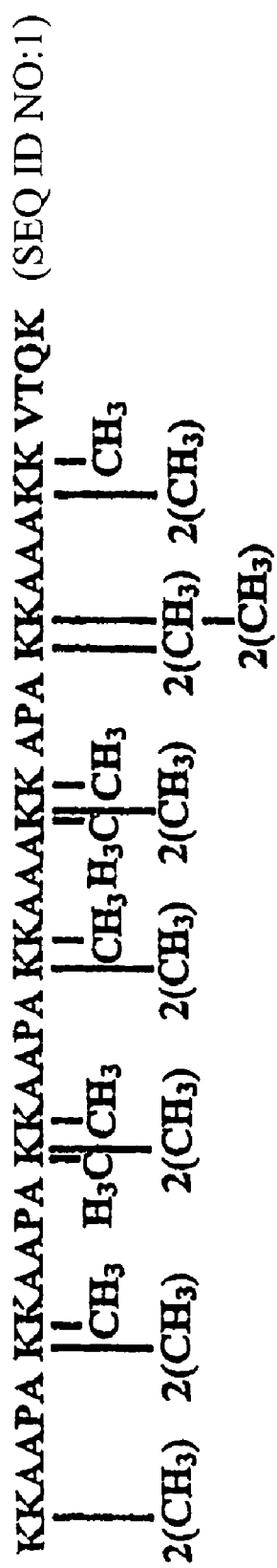
FIG. 2: shows the heparin-binding region of HBHA produced by *M. bovis* BCG or *M. smegmatis* (methylated recombinant HBHA). The lysines modified to mono- or di-methyllysines were identified using the Edman degradation technique.
Figure 3A:
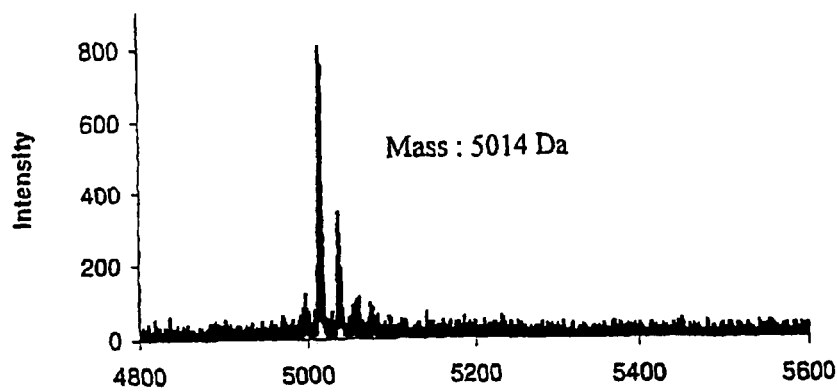
FIG. 3: determination of the weight of the peptide corresponding to the heparin-binding region of non methylated recombinant HBHA and of chemically methylated recombinant HBHA. The different forms of HBHA underwent digestion with Endo-Glu overnight. The fragments corresponding to the heparin-binding binding region were purified by HPLC. The weight of fragments of nonmethylated recombinant HBHA (A), recombinant HBHA chemically methylated for 6 min (B), 31 min (C) and 120 min(D), were analyzed by mass spectroscopy.
Figure 3B:
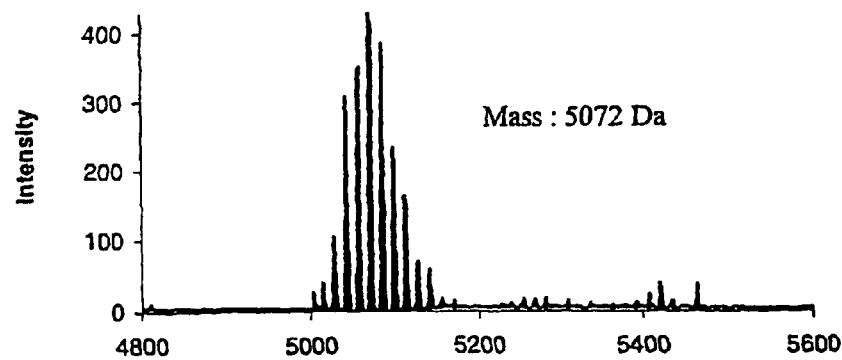
Figure 3C:
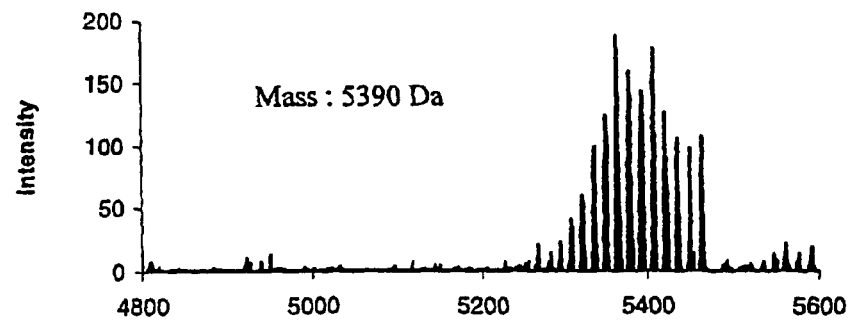
Figure 3D:
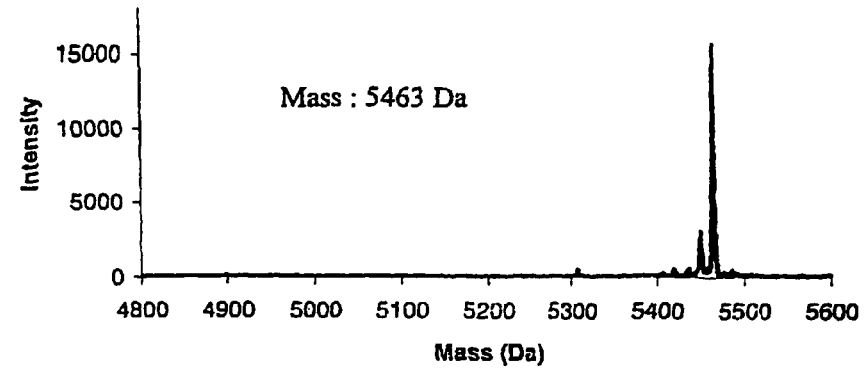

For accurate identification of the modified amino acids, the sequence for the heparin-binding region was determined using the Edman degradation method in accordance with conventional procedures. This study revealed that only the lysines had been modified. Further, of the fifteen lysine residues present in the C-terminal region of HBHA, only two had the standard retention time for lysine. The thirteen other residues had retention times corresponding to glutamine and/or arginine standards. Initially, since (i) mass spectrometry analysis showed that there was an increment of 14 Da between the different fragments of native HBHA, and (ii) only the lysines had been modified, it was hypothesized that the lysines in the C-terminal region could have been methylated, giving mono-, di- or tri-methyllysines. This hypothesis proved to be only partially accurate, however, as no tri-methyllysine had been positively identified in the native HBHA. This verification was made using standard calibration methods corresponding to mono-, di- and tri-methyllysines respectively. The modified lysines had retention times that conformed with those for mono- and di-methyllysine but not tri-methyllysine (FIG. 2).

An amino acid analysis, including the mono-, di- and tri-methyllysine as standards, confirmed this result.

II-3—Chemical Methylation of Recombinant HBHA

Recombinant HBHA was chemically methylated and then underwent mass spectrometrical analysis. As shown in FIG. 3, the mass of the peptide corresponding to the C-terminal region of the recombinant HBHA increased as the chemical methylation advanced.

Figure 4:
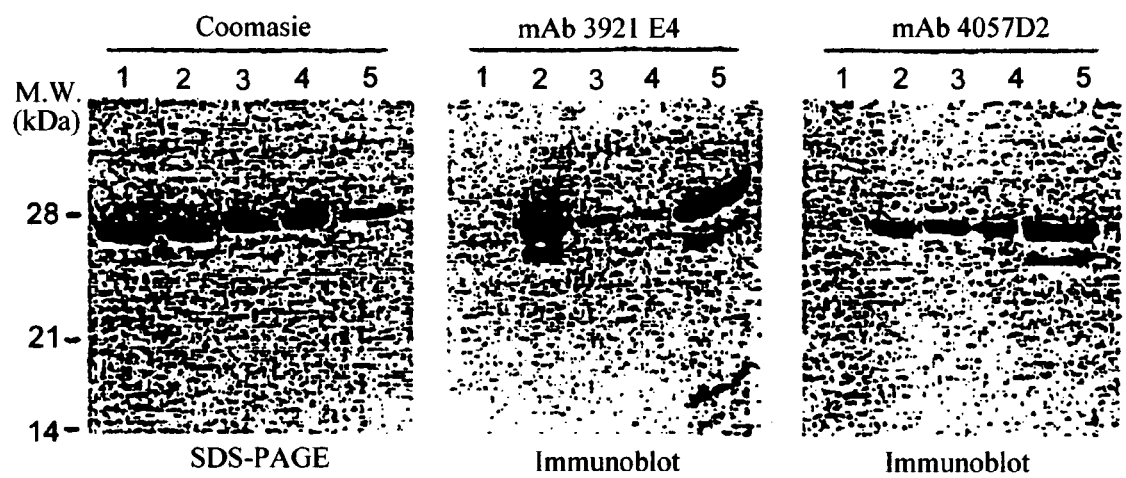
FIG. 4: SDS-PAGE and immunoblot analysis of recombinant HBHA (1), recombinant HBHA chemically methylated for 6 min (2), 31 min (3), 120 min (4) and native HBHA (5). The immunoblot analyses were carried out using two monoclonal antibodies 3921E4 and 4057D2 (Rouse et al, 1991, supra).

Further, the degree of methylation influenced the reactivity of the peptides with the monoclonal antibodies 3921E4 and 4057D2 (Rouse et al, 1991, supra) (FIG. 4). As described previously (Menozzi et al, 1998, supra), recombinant HBHA was not recognized by antibody 4057D2, although it was weakly recognized by antibody 3921E4. In contrast, as shown in FIG. 4, the degree of methylation of the recombinant HBHA affected its affinity for these two antibodies in different manners, showing that methylation of a protein could play an important role in its antigenicity.

II-4—Enzymatic Methylation of Recombinant HBHA

In order to determine whether methylation of the lysines of native HBHA was due to enzymatic activity, an in vitro methylation test specific for recombinant HBHA was carried out using a mycobacterial lysate. Mycobacterial cultures were lysed by sonication. The total lysates, as well as the cytoplasmic and parietal fractions were used as enzymatic sources to attempt to transfer [$^{14}$C]methyl groups from the [$^{14}$C-methyl]AdoMet donor to the acceptor represented by the recombinant HBHA. Incubation of total lysates of *M. tuberculosis, M. bovis* BCG and *M. smegmatis* containing [$^{14}$C-methyl]AdoMet with recombinant HBHA resulted in the incorporation of [$^{14}$C]methyl groups into said HBHA (FIG. 2). In contrast, when the lysates were heated to 95° C., they were no longer capable of catalyzing the transmethylation reaction. Further, the mycobacterial methyltransferase or methyltransferases responsible for methylating the HBHA were thermosensitive.

Isolation of the methyltransferase or methyltransferases was envisaged through different approaches.

In a first case, the proteins present in a mycobacterial lysate were separated by ion exchange chromatography, HPLC or affinity, depending on the fractions capable of catalyzing the transmethylation reaction from [$^{14}$C-methyl]AdoMet onto recombinant HBHA. Such concentration procedure was continued until a sample was obtained in which the methyltransferase or methyltransferases were sufficiently pure to determine its sequence. Then, referring to the known sequence of the genome of *M. tuberculosis* H37Rv (Cole et al, 1998, supra), the gene or genes encoding the methyltransferase or methyltransferases were identified then cloned using techniques known to the skilled person.

A second approach consisted of seeking candidate genes potentially encoding methyltransferases in the genome of *M. tuberculosis* H37Rv on the basis of sequence homology with the known and identified sequence for methyltransferase genes per se in databases. Five candidate genes were selected, namely Rv0208c, Rv0380, Rv1405, Rv1644 and Rv3579. These genes were cloned and expressed in *E. coli*. The products of said genes were then purified and tested for their capacity to methylate recombinant HBHA from a radioactively labeled methyl AdoMet donor.

II-5—Production of HBHA by *M. smegmatis*

It has been demonstrated that *M. smegmatis* does not express HBHA (Pethe et al, 2001, supra). However, it was possible to transfer [$^{14}$C]methyl groups from [$^{14}$C-methyl] AdoMet to recombinant HBHA using a lysate of this microorganism (FIG. 2). It was also suggested that M. smegmatis had the enzymatic machinery responsible for the HBHA transmethylation reaction. With the aim of verifying this hypothesis, the *M. smegmatis* $MC^2155$ strain was transformed with a derivative of plasmid pRR3 containing the hbhA gene (Rv0475) encoding HBHA in *M. bovis* BCG, to obtain the *M. smegmatis* (pRR-hbhA) strain. The production of HBHA was analyzed by Western blot. The HBHA produced by *M. smegmatis* (pRR-hbhA), termed MS-HBHA, was recognized by the monoclonal antibodies 3921E4 and 4057D2, strongly suggesting that this MS-HBHA had been post-translationally modified, like native HBHA from *M. bovis* BCG. The MS-HBHA was purified and underwent hydrolysis by Endo-Glu. Mass spectrometry analysis of the digested products thus obtained and peptide sequence determination of the C-terminal region of the MS-HBHA showed that it effectively had the same type of post-translational modification as the HBHA from *M. bovis*. As a consequence, *M. smegmatis* had an enzymatic machinery that was capable of catalyzing the methylation of recombinant HBHA.

As a result, to carry out the vaccination experiments, native HBHA was alternatively purified from the *M. smegmatis* transformed strain (pRR-hbhA).

II-6—Study of Native HBHA as a Protective Antigen

The immune response generated by native HBHA, and its protective power against infection by *M. tuberculosis*, were tested in the murine model.

These experiments were also carried out using recombinant HBHA in the non methylated and methylated forms.

The immunization protocol was derived from the literature (Brandt et al, 2000, Infect Immun 68: 791-795). The adjuvants DDA and MPL were used in amounts of 150 μg and 25 μg per dose respectively.

Group 1 was vaccinated with the adjuvant alone contained in 200 μl of PBS buffer. Group 2 was vaccinated: with 5 μg of purified native HBHA emulsified in 200 μl of a PBS-adjuvant mixture. Group 3 was vaccinated with 5 μg of native HBHA alone in solution in 200 μl of PBS. The mice received three injections of different preparations at two week intervals. A fourth group (positive control) was vaccinated with a dose of $5 \times 10^5$ CFU of BCG.

Blood was sampled from all of the mice of the different groups ten days after the last injection of the vaccine preparations to test the production of antibodies specific to native HBHA. For each group, IgG assays were carried out on serum mixtures. The antibody titer was defined as corresponding to the maximum dilution of serums giving a value three times higher than the blank. Table 1 below shows a reading of the IgG titers induced per injection of the different preparations.

TABLE 1

|  | Group 1 adjuvant | Group 2 HBHA + adjuvant | Group 3 HBHA | Group 4 BCG |
|---|---|---|---|---|
| total IgG | <10 | 73000 | 5000 | <50 |
| IgG1 | <10 | 580000 | 24000 | <10 |
| IgG2a | <10 | 17000 | 800 | <20 |
| IgG2b | <10 | 8500 | 90 | <10 |
| IgG3 | <10 | 750 | 150 | <10 |

The results show that the mice vaccinated with HBHA (groups 2 and 3) produced large quantities of IgG1 and also produced IgG2a, IgG2b and IgG3. These types of antibodies reflect the generation of a mixed TH1/TH2 response. The presence of the adjuvant (group 2) did not modify the response profile with respect to the HBHA protein alone (group 3). However, said adjuvant could produce about 10 times more of the different IgGs (Table 1).

Figure 5:
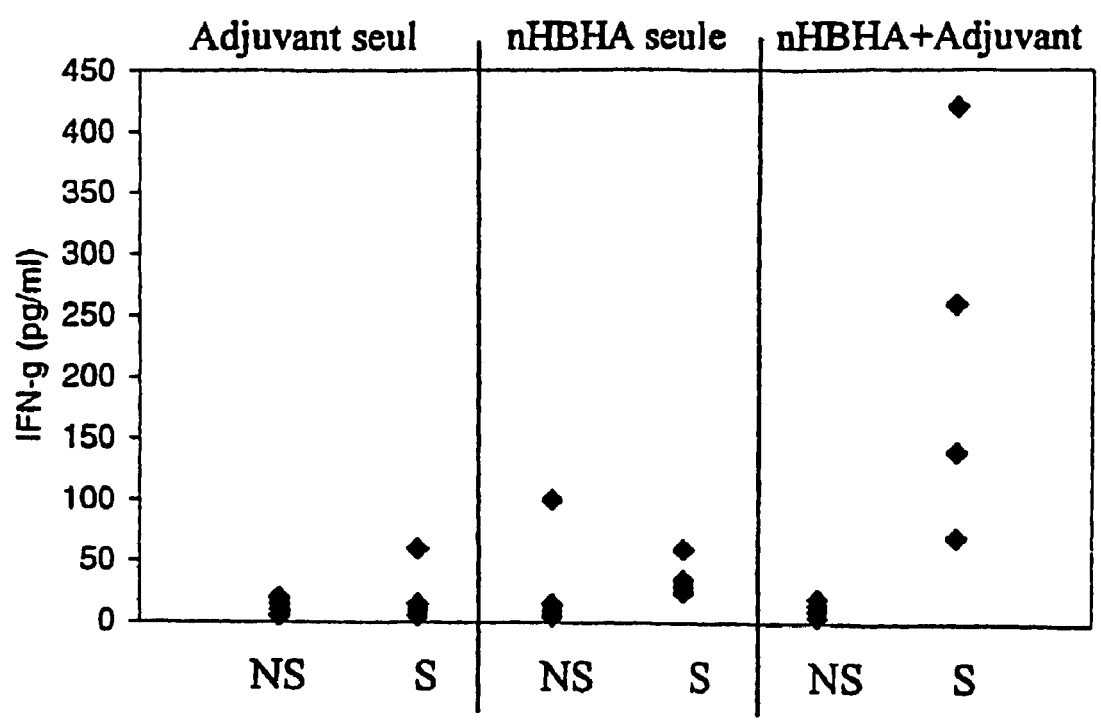
FIG. 5: measure of immune cell response induced by injecting different preparations. Spleen cells from four mice per group were placed in culture ten weeks after the initial immunization. The cells were unstimulated (NS) or stimulated (S) for 72 h with native HBHA (2 µg/ml). The concentration of IFN-γ was then assayed in the culture supernatants.

To test the cell response, four mice per group were sacrificed ten weeks after the first injection. The lymphocytes were collected and stimulated in vitro with native HBHA. After stimulation, the IFN-γ production was tested. As shown in FIG. 5, only the lymphocytes purified from mice of group 2, vaccinated with native HBHA associated with adjuvant, produced IFN-γ specific to said HBHA.

Finally, experiments were carried out with the aim of testing the protective power of native HBHA against an infection with M. tuberculosis. Group 3, vaccinated with HBHA alone, was set aside in favor of group 2, given that the immune response, both humoral (Table 1) and cellular (FIG. 5) appeared to be of better quality in group 2 in the light of the experimental results. Ten weeks after the first injection of the vaccine preparations, mice were intravenously infected with $10^5$ CFU of M. tuberculosis. Four mice per group were sacrificed six weeks after infection to determine the number of CFUs present in the different mouse organs. The bacterial charge was determined in the liver, spleen and lungs of the animals. Resistance was defined as the difference in bacterial charge, expressed as the $\log_{10}$, between the control group 1, vaccinated with adjuvant alone, and groups 2 and 4, respectively vaccinated with HBHA associated with adjuvant and with BCG. Table 2 below shows the efficacy of the protection induced by the different immunizations.

TABLE 2

|  | Liver | | Spleen | | Lungs | |
|---|---|---|---|---|---|---|
|  | CFU ($\log_{10}$) | Resistance | CFU ($\log_{10}$) | Resistance | CFU ($\log_{10}$) | Resistance |
| Group 1 adjuvant | 5.60 ± 0.20 |  | 5.85 ± 0.21 |  | 5.27 ± 0.25 |  |
| Group 2 HBHA + adjuvant | 4.66 ± 0.35 | 0.94 | 5.00 ± 0.04 | 0.85 | 4.34 ± 0.17 | 0.93 |
| Group 4 BCG | 4.41 ± 0.20 | 1.19 | 4.68 ± 0.25 | 1.17 | 4.45 ± 0.20 | 0.82 |

Determining the CFUs showed that the immune response caused by native HBHA was capable of rendering the mouse partially resistant to infection by M. tuberculosis. The observed resistance was of the same order of magnitude, both for the native HBHA and the prior art reference vaccine, namely BCG. As a result, injection of native HBHA would protect the mouse from infection with M. tuberculosis, in proportions close to those for the BCG vaccine.

This experiment was carried out using the methylated and nonmethylated forms of the recombinant HBHA to compare the level and efficacy of the induced protection with that observed with native HBHA. Thus, methylated recombinant HBHA, in that it is immunogenic, causes resistance in animals to an infection with M. tuberculosis that is as effective as that induced by native HBHA.

In a further aspect, the present invention provides a sub-unit vaccine intended for the treatment of mycobacterial infections and comprising native HBHA in its formulation.

Within the context of the production of vaccine compositions on an industrial scale, it is politic to use genetically recombinant producting organisms which are often more advantageous than wild producting organisms in that the former can easily be transformed by the nucleotide sequences of the latter, encoding the protein or proteins of interest, and in that they are carefully selected, in particular for their harmlessness and their readily controllable growth parameters, and so there is no need to invest in expensive specialized equipment. For this reason, a preferred aspect of the invention concerns a sub-unit vaccine for the treatment of mycobacterial infections advantageously characterized in that it comprises in its formulation methylated HBHA in its recombinant version, i.e. produced by a recombinant host cell meticulously selected to satisfy industrial and safety requirements.

The invention claimed is:

1. An immunogenic composition, consisting of, as an active principle, a pure methylated heparin-binding hemagglutinin (HBHA) protein in a pharmaceutically acceptable formulation, and one or more adjuvants.

2. A method for treating mycobacterial infections said method comprising administering to a mammal in need of said treatment the immunogenic composition of claim 1.

3. An immunogenic composition according to claim 1, wherein said pure methylated heparin-binding hemagglutinin (HBHA) protein is obtained by a method comprising a final purification step consisting of a reverse phase HPLC.

4. The immunogenic composition according to claim 1, wherein said HBHA antigen is from *M. bovis* or *M. tuberculosis*.

5. The immunogenic composition according to claim 4, consisting of between 0.1 and 20 µg of HBHA protein per dose.

6. The immunogenic composition according to claim 5, consisting of 5 µg of HBHA protein per dose.

7. An immunogenic recombinant protein, comprising a methylated expression product of a nucleotide sequence encoding a heparin-binding hemagglutinin (HBHA) mycobacterial antigen.

8. The immunogenic recombinant protein according to claim 7, wherein the nucleotide sequence encodes a heparin-binding region of the HBHA.

9. The immunogenic recombinant protein according to claim 8, wherein methyl groups are carried by lysine residues located in a heparin-binding region of the HBHA.

10. The immunogenic recombinant protein according to claim 9, wherein the lysine residues are mono- or di-methylated.

11. The immunogenic recombinant protein according to claim 8, wherein methyl groups are carried by all or a portion of the lysine residues located in the heparin-binding region of the HBHA.

12. The immunogenic recombinant protein according to claim 7, wherein methyl groups are carried by lysine residue located in a heparin-binding region of the HBHA.

13. The immunogenic recombinant protein according to claim 12, wherein the lysine residues are mono- or di-methylated.

14. The immunogenic recombinant protein according to claim 13, wherein the methyl groups are carried by all or a portion of the lysine residues located in the heparin-binding region of the HBHA.

15. The immunogenic recombinant protein according to claim 12, wherein the methyl groups are carried by all or a portion of the lysine residues located in the heparin-binding region of the HBHA.

16. The immunogenic recombinant protein according to claim 7, wherein said protein is recognized by the monoclonal antibody 4057D2.

17. The immunogenic recombinant protein according to claim 7, obtained by transforming *M. bovis* BCG, *M. smegmatis* or *M tuberculosis*.

18. The immunogenic recombinant protein according to claim 7, wherein HBHA protein is from *M. bovis* or *M. tuberculosis*.

19. An immunogenic composition consisting of between 0.1 and 20 µg of the methylated recombinant protein according to claim 7 per dose, and one or more adjuvants.

20. A method for treating mycobacterial infections said method comprising administering to a mammal in need of said treatment an immunogenic composition consisting of the methylated recombinant protein according to claim 7.

* * * * *

UNITED STATES PATENT AND TRADEMARK OFFICE
CERTIFICATE OF CORRECTION

| | | |
|---|---|---|
| PATENT NO. | : 7,829,103 B2 | Page 1 of 1 |
| APPLICATION NO. | : 10/847606 | |
| DATED | : November 9, 2010 | |
| INVENTOR(S) | : Pethe et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 842 days.

Signed and Sealed this
Third Day of May, 2011

David J. Kappos
*Director of the United States Patent and Trademark Office*